United States Patent
Fujita (10) Patent No.: US 9,316,625 B2
(45) Date of Patent: Apr. 19, 2016

(54) MASS SPECTROMETER

(71) Applicant: SHIMADZU CORPORATION, Kyoto-shi, Kyoto (JP)

(72) Inventor: Shinjiro Fujita, Kameoka (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/429,025

(22) PCT Filed: Sep. 20, 2012

(86) PCT No.: PCT/JP2012/074002
§ 371 (c)(1),
(2) Date: Mar. 18, 2015

(87) PCT Pub. No.: WO2014/045360
PCT Pub. Date: Mar. 27, 2014

(65) Prior Publication Data
US 2015/0219607 A1    Aug. 6, 2015

(51) Int. Cl.
*H01J 49/00*    (2006.01)
*G01N 30/72*    (2006.01)
(Continued)

(52) U.S. Cl.
CPC ........ *G01N 30/7233* (2013.01); *H01J 49/0027* (2013.01); *H01J 49/025* (2013.01); *H01J 49/0431* (2013.01); *H01J 49/10* (2013.01)

(58) Field of Classification Search
CPC ... G01N 30/7233; H01J 49/10; H01J 49/0431
USPC ............................................... 250/282, 288
See application file for complete search history.

(56) References Cited

U.S. PATENT DOCUMENTS

2002/0162959 A1* 11/2002 Itoi .............................. 250/292
2009/0008548 A1* 1/2009 Yamaguchi ................. 250/288
2009/0230297 A1* 9/2009 Mizutani ..................... 250/281

FOREIGN PATENT DOCUMENTS

JP    2000-357487 A    12/2000
JP    2002-329474 A    11/2002
(Continued)

OTHER PUBLICATIONS

International Search Report of PCT/JP2012/074002, dated Dec. 25, 2012. [PCT/ISA/210].
(Continued)

*Primary Examiner* — Michael Maskell
(74) *Attorney, Agent, or Firm* — Sughrue Mion, PLLC (57) ABSTRACT

Every time a target sample is injected from an injector (12) of an LC unit (1) and a mass spectrometry for a target component in the sample is performed, a CD voltage applied to a conversion dynode of an ion detector (29) is switched. For each of the multiple CD-voltage levels, a data collector (32) collects noise data during a period of time where no component is present and intensity data of an ion originating from the target component, while the SN ratio calculator (33) calculates an SN ratio. After the actual measurement is completed, an optimum CD voltage determiner (34) compares the SN ratios calculated for each CD voltage, finds the CD voltage which gives the highest SN ratio, and stores this voltage in an optimum CD voltage memory (42) as an optimum CD voltage for the analysis conditions at that point in time and for the m/z of the analysis target. According to this method, even when the flow rate of the mobile phase is particularly high or when a hard-to-vaporize mobile phase is used, the CD voltage is appropriately set and a detection signal is obtained with high SN ratios.

3 Claims, 3 Drawing Sheets

(51) Int. Cl.
*H01J 49/02* (2006.01)
*H01J 49/04* (2006.01)
*H01J 49/10* (2006.01)

(56) References Cited

FOREIGN PATENT DOCUMENTS

| | | | |
|---|---|---|---|
| JP | 2007-258179 | A | 10/2007 |
| JP | 2009-266445 | A | 11/2009 |
| JP | 2011-86403 | A | 4/2011 |
| JP | 4858614 | B2 | 1/2012 |
| WO | 2009/011011 | A1 | 1/2009 |

OTHER PUBLICATIONS

Japanese Office Action corresponding to Japanese Patent Application No. 2014-536467, dated Aug. 25, 2015.

* cited by examiner

MASS SPECTROMETER

CROSS REFERENCE TO RELATED APPLICATIONS

This application is a National Stage of International Application No. PCT/JP2012/074002 filed Sep. 20, 2012, the contents of all of which are incorporated herein by reference in their entirety.

TECHNICAL FIELD

The present invention relates to a mass spectrometer, and more specifically, to a mass spectrometer using an ion detector consisting of a conversion dynode and a secondary electron multiplier combined together.

BACKGROUND ART

In mass spectrometers, secondary electron multipliers are commonly used as the detector for detecting ions (see Patent Literature 1). A secondary electron multiplier has a plurality of dynodes arranged in a cascade form. When an incident ion hits the first dynode, secondary electrons are released from this dynode, which are subsequently and repeatedly multiplied. The secondary electrons thus increased in quantity are made to enter a collector and be converted into a current signal. This signal is extracted as the detection signal.

To apply an ion-accelerating voltage to each of the dynodes, a certain level of detection voltage is normally applied to the secondary electron multiplier. However, even if this detection voltage is maintained at the same level, the detection sensitivity of the secondary electron multiplier changes depending on the mass-to-charge ratio of the ion; in particular, the sensitivity becomes low at high mass-to-charge ratios. The reason for this is as follows: When introduced into an ion detector, every ion is given the same amount of kinetic energy $E$ ($=eV_0$). Meanwhile, the speed $v$ of the ion is given by $v=(2E/m)^{1/2}$, which means that an ion having a higher mass m travels at a lower speed v than an ion having a lower mass m. Since the efficiency of conversion from ions to secondary electrons depends on the speed v of the ion, an ion having a high mass m can produce a smaller amount of secondary electrons than an ion having a low mass m, which results in a decrease in the detection sensitivity.

To address this problem, and particularly, to improve the sensitivity to the high-mass ions, a technique is often adopted in which a conversion dynode with a high level of voltage applied is placed in front of the secondary electron multiplier so that ions initially impinge on this conversion dynode and the thereby produced secondary electrons are introduced into and detected by the secondary electron multiplier. Applying a higher level of voltage to the conversion dynode improves the detection sensitivity. Accordingly, the voltage applied to the conversion dynode (which is hereinafter called the "CD voltage") is normally set at the highest possible level within the range where no abnormal electric discharge occurs.

Basically, the CD voltage is maintained at the same level, although it is possible to lower the CD voltage and decrease the gain when the detector may possibly be saturated due to an excessive amount of ions, as described in Patent Literature 2.

CITATION LIST

Patent Literature

Patent Literature 1: JP 2000-357487 A
Patent Literature 2: JP 4858614 B

SUMMARY OF INVENTION

Technical Problem

A mass spectrometer in which the previously described combination of the conversion dynode and the secondary electron multiplier is used as the ion detector has the following problem.

In a liquid chromatograph mass spectrometer (LC/MS), an atmospheric pressure ion source, such as electrospray ionization (ESI) or atmospheric pressure chemical ionization (APCI), is used. In these types of ion sources, ions originating from a target component are desorbed from a solvent (mobile phase) and exclusively introduced into a mass analyzer, such as a quadrupole mass filter. Usually, the solvent turns into vapor and is removed by the exhausting action of a vacuum pump. However, when the solvent is a liquid that is difficult to vaporize or when the droplets of the solvent formed in the atmospheric pressure ion source are large in size, some droplets which have not been removed may accidentally be introduced into the mass analyzer. For example, when water is used as the mobile phase in a liquid chromatograph (LC), some droplets of the water will be introduced into the mass analyzer since water is much less likely to be vaporized than organic solvents.

Most of those droplets are neutral and can pass through the separating field (e.g. a quadrupole electric field) created by the mass analyzer, without being affected by this field. If those droplets reach the conversion dynode, the solvent becomes exposed to the electric field created by the high CD voltage of several kV applied to the conversion dynode and turns into ions, which will be eventually detected as noise. As a result, the SN ratio of the detection signal deteriorates. The magnitude of the aforementioned noise originating from the solvent does not only depend on the kind of mobile phase used in the LC but also on the mobile-phase conditions as well as on the CD voltage. For example, even if the kind of mobile phase is the same, if its flow rate is increased, an accordingly greater amount of droplets are sent into the mass analyzer and the noise tends to be larger in magnitude. Similarly, even if the amount of solvent droplets reaching the conversion dynode is the same, if the CD voltage is increased, the ionization of the solvent is promoted and the noise tends to be larger in magnitude.

As noted earlier, it has been common practice to set the CD voltage at the highest possible level to improve the detection sensitivity to the high-mass ions. However, in some cases, increasing the CD voltage increases the noise. Furthermore, as compared to the case of the high-mass ions, increasing the CD voltage is less effective in improving the signal intensity of the low-mass ions. Therefore, contrary to the expectation, increasing the CD voltage may possibly lower the SN ratio of the detection signal.

The present invention has been developed to solve such a problem, and its objective is to increase the SN ratio of the detection signal and improve the analysis accuracy in a mass spectrometer using an ion detector consisting of a conversion dynode and a secondary electron multiplier combined together.

Solution to Problem

The present invention aimed at solving the previously described problem is a mass spectrometer having: an ion source for ionizing a component in a sample; a mass analyzer for separating ions generated by the ion source according to their mass-to-charge ratios; and an ion detector for detecting the ions separated by the mass analyzer, the ion detector having a conversion dynode for converting ions into electrons and a secondary electron multiplier for multiplying and detecting the electrons, the mass spectrometer including:

a) a voltage supplier for applying high voltage to the conversion dynode;

b) an analysis executer for changing the voltage applied to the conversion dynode by the voltage supplier to a plurality of levels, and for obtaining, for every change in the voltage applied to the conversion dynode, a noise signal under an analysis condition at that point in time and a detection signal corresponding to an ion originating from a target component; and c) an optimum voltage setter for calculating an SN ratio based on the noise signal and the detection signal obtained by the analysis executer for each different level of the applied voltage, and for determining, based on the calculated result, the voltage to be applied to the conversion dynode in an analysis of the target component.

In the mass spectrometer according to the present invention, the analysis executer controls the voltage supplier so that a plurality of the previously determined levels of voltage will be sequentially applied to the conversion dynode. Concurrently, for every change in the applied voltage, the analysis executer obtains a noise signal under the analysis condition at that point in time and a detection signal corresponding to an ion originating from the target component.

Applying a different voltage to the conversion dynode changes the efficiency of the conversion from ions to electrons by the conversion dynode, which causes a change in the detection signal even when the same amount of ions originating from the target component is constantly entering the ion detector. Meanwhile, a change in the voltage applied to the conversion dynode also causes a change in the strength of the electric field near the conversion dynode, which causes a change in the generation efficiency of unwanted ions originating from the solvent if there are droplets of the sample solvent or the like entering the ion detector together with the ions originating from the target component. Thus, applying a different voltage to the conversion dynode causes a change in the level of the noise signal. Given this fact, the optimum voltage setter conducts an actual analysis and calculates an SN ratio based on the level of the noise signal and that of the detection signal obtained for each different level of the applied voltage. Then, based on the calculated result, the optimum voltage setter finds a voltage at which the highest or nearly highest SN ratio is achieved, and determines that voltage as the optimum voltage to be applied to the conversion dynode in an analysis of the target component. Thus, an appropriate conversion-dynode voltage for an analysis of the target component is determined from the viewpoint of the SN ratio.

The problem to be addressed in the mass spectrometer according to the present invention, i.e. the noise signal whose level varies depending on the conversion-dynode voltage, arises from the solvent droplets reaching the conversion dynode without being removed in the course of their travel from the ion source to the conversion dynode. Accordingly, the present invention is particularly useful when applied in a mass spectrometer having an atmospheric pressure ion source for ionizing a component in a sample in liquid form.

Examples of the atmospheric pressure ion source include electrospray ionization sources, atmospheric pressure chemical ionization sources, and atmospheric pressure photo ionization sources.

Furthermore, the mass spectrometer according to the present invention may preferably be configured so that a liquid sample separated into components by a liquid chromatograph is introduced into the atmospheric pressure ion source. In this configuration, the aforementioned analysis condition includes at least the kind of mobile phase used in the liquid chromatograph and the flow rate (or flow velocity) of the mobile phase. That is to say, the analysis executer obtains the noise signal and the detection signal corresponding to an ion originating from the same kind of target component while changing the conversion-dynode voltage to a plurality of levels under the condition that at least the kind of mobile phase is the same and the flow rate (or flow velocity) of the mobile phase is the same.

Liquid chromatographs can temporally separate a plurality of target components contained in a sample. Therefore, it is possible to determine, for each target component, a conversion-dynode voltage that is optimum or nearly optimum in terms of the SN ratio by obtaining the detection signal under a plurality of levels of conversion-dynode voltage at each of the points in time (i.e. retention times) at which the target components are respectively eluted. When a liquid chromatographic mass spectrometry of a sample containing those target components is performed, all the target components can be detected with high SN ratios by switching the conversion-dynode voltage for each target component based on the conversion-dynode voltages which have been determined in the previously described manner.

In the case of a SIM (selected ion monitoring) or MRM (multiple reaction monitoring) measurement aimed at an ion originating from each target component, it is possible to switch the conversion-dynode voltage for each ion having a different mass-to-charge ratio during the SIM or MRM measurement by setting the measurement conditions so that a period of time equal to or longer than the time required for switching the conversion-dynode voltage (including not only a time for switching the voltage but also a time for allowing the detection signal to become stable after the switching) is provided between the time segments assigned to the actual measurement. By this method, all the target components can be detected with high SN ratios.

Advantageous Effects of the Invention

By the mass spectrometer according to the present invention, the SN ratio of the ion detection signal can be higher than ever before, so that a mass spectrometry with high accuracy and high sensitivity can be performed. Particularly, in a liquid chromatograph mass spectrometer, when the noise signal originating from the droplets reaches a high level, i.e. when the flow rate of the mobile phase is high (typically, 1 mL/min or higher) and the mass-to-charge ratio of the ion of the target component is low (typically, m/z 200 or lower), decreasing the conversion-dynode voltage produces a noticeable effect of noise reduction while causing only a small decrease in the ion intensity, so that a considerable improvement in the SN ratio can be expected.

DESCRIPTION OF EMBODIMENTS

Figure 1:
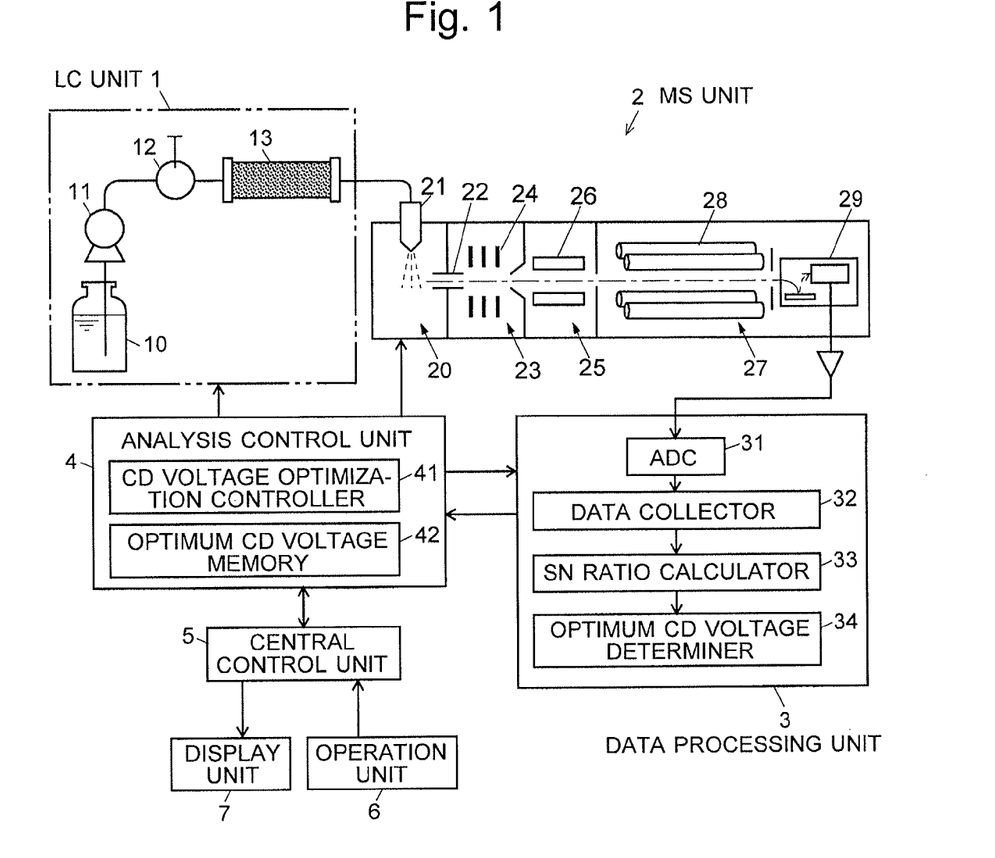
FIG. 1 is an overall configuration diagram of a mass spectrometer which is one embodiment of the present invention.
Figure 2:
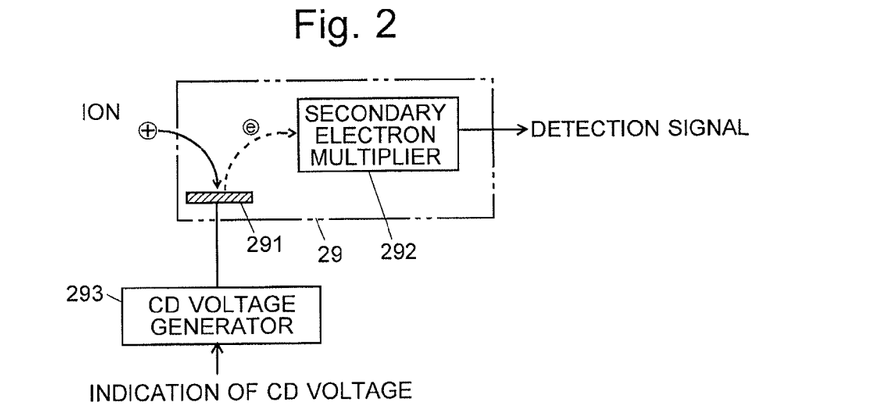
FIG. 2 is a configuration diagram of the ion detector in FIG. 1.

One embodiment of the mass spectrometer according to the present invention is hereinafter described in detail with reference to the attached drawings. FIG. 1 is an overall configuration diagram of a liquid chromatograph mass spectrometer (LC/MS) of the present embodiment, and FIG. 2 is a configuration diagram of the ion detector in FIG. 1.

The LC/MS of the present embodiment includes an LC unit 1 and an MS unit 2. In the LC unit 1, a mobile phase stored in a mobile phase container 10 is sent to a column 13 at an almost constant flow rate by a liquid-sending pump 11. When a certain amount of sample liquid is injected from an injector 12, the sample liquid is carried by the mobile phase into the column 13. While passing through this column 13, various components contained in the sample liquid are temporally separated and eluted from the exit of the column 13.

The MS unit 2 has the configuration of a multi-stage differential pumping system provided with an electrospray ionization source, which is a type of atmospheric pressure ion source. The liquid sample coming from the exit of the column 13 of the LC unit 1 is electrostatically sprayed from a spray nozzle 21 of the electrospray ionization source into an ionization chamber 20 maintained at approximately atmospheric pressure. The electrically charged droplets thus sprayed come in contact with the surrounding air and turn into smaller droplets, causing the solvent in the droplets to vaporize. During this process, the components contained in the droplets are ionized. The ions thus derived from the sample components are mixed with fine droplets from which the solvent has been incompletely vaporized, and this mixture is drawn into a desolvation tube 22 due to the pressure difference between the two ends of this tube 22, to be sent into a first intermediate vacuum chamber 23. Since the desolvation tube 22 is heated, the vaporization of the solvent in the droplets is further promoted inside the desolvation tube 22 and the ionization is thereby promoted. The ions are conveyed through a first ion guide 24 in the first intermediate vacuum chamber 23 as well as a second ion guide 26 in a second intermediate vacuum chamber 25 located in the next stage, into an analysis chamber 27 maintained at a high degree of vacuum.

The analysis chamber 27 contains a quadrupole mass filter 28, which is a mass analyzer, and an ion detector 29. Among the ions introduced into the quadrupole mass filter 28, only an ion having a specific mass-to-charge ratio is selectively allowed to pass through the quadrupole mass filter 28, to be received and detected by the ion detector 29. The detection signal produced by the ion detector 29 is sent to a data processing unit 3, which includes an A/D converter 31 and other elements. Based on the obtained data, the data processing unit 3 creates a mass spectrum, mass chromatogram, total ion chromatogram or the like. An analysis control unit 4 controls the LC unit 1, MS unit 2 and data processing unit 3 to perform an LC/MS analysis. A central control unit 5, with an operation unit 6 and a display unit 7 attached, provides a user interface. The central control unit 5 also acts as a general manager for performing instructions and controls related to the analysis.

The functions of the central control unit 5, as well as a portion of the functions of the data processing unit 3 and the analysis control unit 4, can be embodied by executing, on a personal computer, a dedicated controlling and processing software program installed in the same computer.

To perform the CD voltage optimization process (which will be described later), the data processing unit 3 includes a data collector 32, an SN ratio calculator 33 and an optimum CD voltage determiner 34 as its functional blocks, while the analysis control unit 4 includes a CD voltage optimization controller 41 and an optimum CD voltage memory 42 as its functional blocks.

As shown in FIG. 2, the ion detector 29 has a conversion dynode 291 for converting ions into electrons and a secondary electron multiplier 292 which includes a multi-stage dynode (not shown) for multiplying electrons and a collector (not shown) for converting electrons into current signals. A predetermined level of direct-current high voltage is applied from a CD voltage generator 293 to the conversion dynode 291 as the CD voltage. Although another direct-current voltage is applied to the secondary electron multiplier 292, the functional block that should be provided for this purpose is omitted from the drawing.

As described earlier, in a conventional and common type of mass spectrometer, the level of the CD voltage applied to the conversion dynode 291 is fixed. By contrast, in the LC/MS of the present embodiment, the level of this CD voltage is optimized according to analysis conditions and/or other factors. More specifically, the CD voltage is optimized in the process of detecting an ion originating from a target component so that the SN ratio of the thereby obtained detection signal will be at the highest possible level (or close to that level). The control and process steps for optimizing the CD voltage will be hereinafter described.

Initially, a user prepares a target sample to be actually analyzed, and enters and sets analysis conditions through the operation unit 6. The analysis conditions include: LC separation conditions, such as the flow rate (or flow velocity) of the mobile phase in the LC unit 1, the composition of the mobile phase (solvent) and the gradient conditions; the retention time of the target component in the sample (if it is known); the retention time of the target component to be analyzed in the MS unit 2 (if it is known); and the mass-to-charge ratio m/z of an ion originating from the target component. When the mass-to-charge ratio m/z of the ion which will originate from the target component is unknown and the CD voltage needs to be optimized, a scan-mode LC/MS analysis can be previously performed to determine the mass-to-charge ratio of the ion which will originate from the target component.

When the user enters a command for executing the CD voltage optimization process through the operation unit 6, the central controller 5 instructs the CD voltage optimization controller 41 to begin controlling each section to perform the CD voltage optimization process. That is to say, the LC 1 is controlled so as to perform an LC analysis a plurality of times on the same target sample according to the LC separation conditions previously entered and set, while the CD voltage generator 293 of the MS unit 2 is controlled so as to sequentially switch the CD voltage to each of the predetermined levels for each execution of the LC/MS analysis. In the present example, the CD voltage is sequentially changed to five levels: −1 kV, −2 kV, −3 kV, −5 kV and −6 kV. The voltage values and the number of voltage levels can be appropriately changed. The detection target in the present example is a positive ion, and therefore, the CD voltage has the negative polarity. If the detection target is a negative ion, the CD voltage will have the positive polarity.

Under the control of the CD voltage optimization controller 41, the CD voltage generator 293 initially applies a CD voltage of −1 kV, i.e. the voltage having the smallest absolute value, to the conversion dynode 291. In the LC unit 1, the target sample is injected from the injector 12 into the mobile phase supplied by the liquid-sending pump 11, and this sample is carried into the column 13. Meanwhile, under the aforementioned CD-voltage condition, the MS unit 2 performs a mass spectrometry for an ion or ions originating from the target sample contained in the liquid sample eluted from the exit of the column 13.

Figure 3:
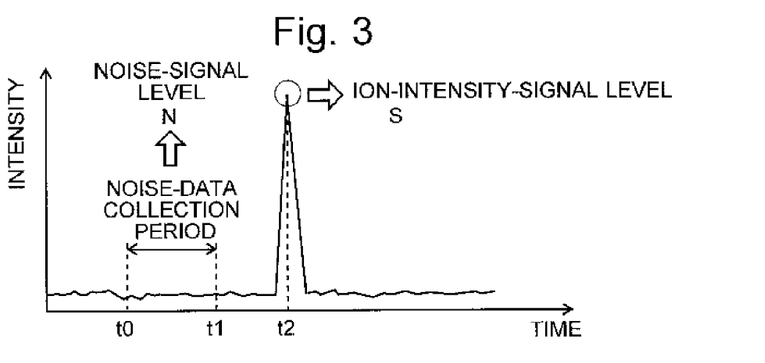
FIG. 3 is a chromatogram for explaining the operation of the mass spectrometer of the present embodiment during the CD voltage optimization process.

Suppose that the target sample contains only a single target component. In this case, a mass chromatogram obtained at the mass-to-charge ratio of the ion originating from that target component will be as shown in FIG. 3. For a certain period of time from the sample injection point, the target component is not contained in the liquid sample eluted from the column 13, so that the ion intensity is constantly at low levels. As the retention time of the target component approaches, the liquid sample containing the target sample begins to be introduced into the spray nozzle 21. Therefore, the ions originating from the target component, which are mainly produced inside the ionization chamber 20, are introduced into the quadrupole mass filter 28, pass through the same mass filter 28 and reach the ion detector 29. As a result, a peak having an ion intensity corresponding to the content of the target component appears on the mass chromatogram, as shown in FIG. 3.

If an impurity or similar component other than the target component is contained in the liquid sample introduced into the spray nozzle 21, an ion or ions originating from that component will also be generated. However, those ions cannot pass through the quadrupole mass filter 28, and therefore, will not affect the detection signal produced by the ion detector 29. However, if the solvent in the droplets sprayed from the spray nozzle 21 is insufficiently vaporized and the solvent droplets with no electric charge are introduced intact into the quadrupole mass filter 28, those droplets will travel directly and reach the ion detector 29. Since high voltage is applied to the conversion dynode 291 and a strong electric field is thereby created around the conversion dynode 291, droplets which have entered this electric field will turn into ions due to the ionization effect. If the unwanted ions thus generated impinge on the conversion dynode 291, electrons will be released, so that a noise due to the solvent droplets will occur in the detection signal of the ion detector 29.

This noise is almost constantly generated from the beginning of the analysis, including the period of time where the target component is present. Accordingly, the data collector 32 in the data processing unit 3 collects noise data over an appropriate period of time within the time range between the beginning of the analysis and the beginning of the elution of the target component. For example, as shown in FIG. 3, a period of time (t0-t1) which begins at point t0 which is later than the beginning of the analysis by a predetermined period of time and ends at point t1 which is earlier than the retention time t2 by a predetermined period of time is designated as the noise-data collection period. During this period, the detection signals produced by the ion detector 29 are digitized by the A/D converter 31 and the obtained pieces of data are collected. Besides, the data collector 32 also collects the data showing the maximum ion intensity in the vicinity of the retention time t2. The noise-data collection period can be arbitrarily set within a range where no ion originating from the target component is present.

Based on a plurality of data collected in the noise-data collection period, the SN ratio calculator 33 calculates the noise-signal level N. The noise-signal level can be calculated by any of the various methods conventionally used. The SN ratio calculator 33 calculates the SN ratio of the ion-intensity-signal level S (which is computed from the data of the maximum ion intensity) to the noise-signal level N, links the calculated value with the CD voltage at that point in time, and temporarily stores the result in an internal memory.

Subsequently, the CD voltage generator 293 changes the CD voltage applied to the conversion dynode 291 to −2 kV. Then, as in the previously described LC/MS analysis conducted under the CD-voltage condition of −1 kV, the target sample is injected into the mobile phase and separated into components by the column 13 under the predetermined LC separation conditions, while the MS unit 2 performs a mass spectrometry, under the aforementioned CD-voltage condition, for an ion originating from the target component contained in the liquid sample eluted from the exit of the column 13. The data collector 32 collects data based on the detection signals obtained with the ion detector 29, and the SN ratio calculator 33 calculates the SN ratio obtained under the CD voltage at that point in time and stores the result.

The previously described LC/MS analysis and processes are similarly repeated, with the CD voltage sequentially changed to −3 kV, −5 kV and −6 kV. Thus, the SN ratio for the ion originating from the target component is obtained for each of the five CD voltage levels of −1 kV, −2 kV, −3 kV, −5 kV and −6 kV. Even if the same kind of ion is analyzed under the same LC separation conditions, the noise-signal level N changes with the CD voltage, since the generation efficiency of unwanted ions around the conversion dynode 291 changes with the CD voltage. Naturally, the ion-intensity-signal level S corresponding to the ion originating from the target component also changes with the CD voltage, since the efficiency of conversion from ions to electrons by the conversion dynode 291 also changes with the CD voltage.

Figure 4:
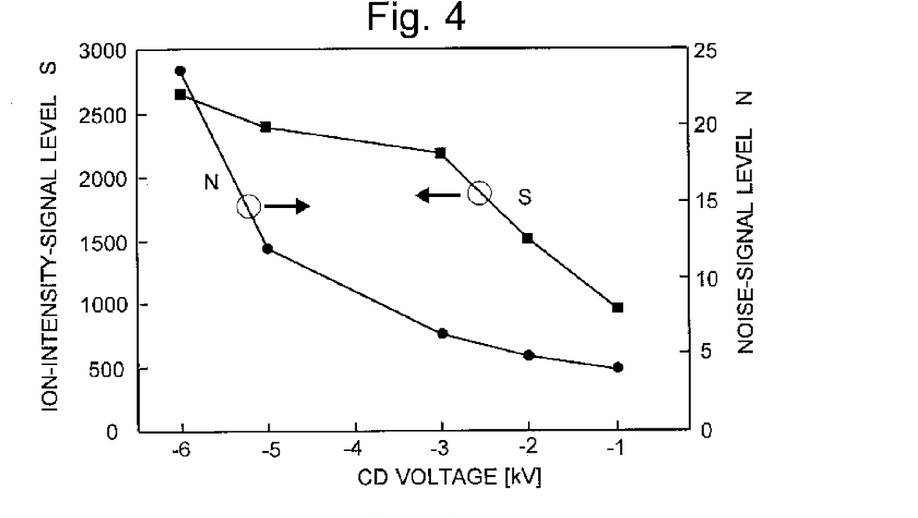
FIG. 4 is an example of the ion intensity signal and the noise signal actually measured for various levels of the CD voltage.
Figure 5:
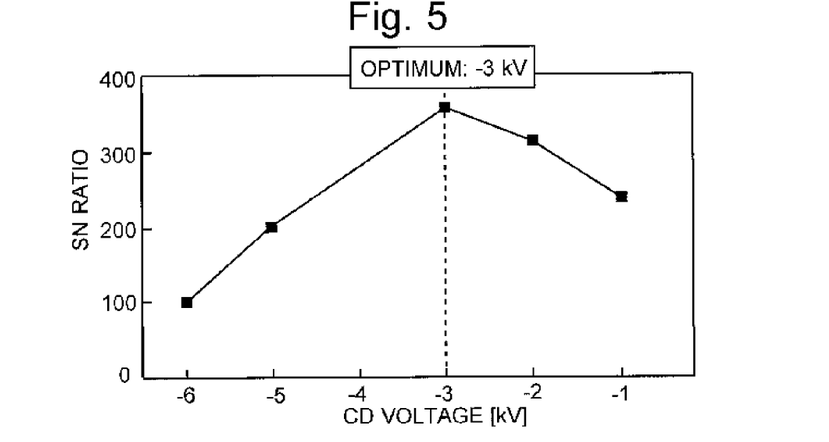
FIG. 5 is a graph showing the SN ratio based on the measured result shown in FIG. 4.

FIG. 4 shows one example of the ion-intensity-signal level S and the noise-signal level N actually measured for an ion under predetermined LC separation conditions, and FIG. 5 shows the relationship between the SN ratio calculated from the result of FIG. 4 and the CD voltage. As can be seen in FIG. 4, although both the ion-intensity-signal level S and the noise-signal level N becomes higher as the absolute value of the CD voltage increases, their degrees of increase are not the same. Therefore, as shown in FIG. 5, the SN ratio is maximized at a certain level of CD voltage, which is −3 kV in the present example. Setting the CD voltage at any level higher or lower than that level lowers the SN ratio.

After the entire analysis is completed, the optimum CD voltage determiner 34 in the data processing unit 3 reads and compares the SN ratios which have been linked with the corresponding CD voltages and stored in the previously described manner, to find the CD voltage at which the SN ratio is maximized. The CD voltage thus found is judged to be the optimum CD voltage for the analysis conditions, the mass-to-charge ratio of the ion and other conditions at that point in time, and is stored in the optimum CD voltage memory 42 of the analysis control unit 4. Subsequently, when an LC/MS analysis for the same target sample is performed under the same analysis conditions, the analysis control unit 4 indicates to the CD voltage generator 293 the CD voltage stored in the optimum CD voltage memory 42, and instructs it to perform the analysis under that CD voltage. As a result, a detection signal with the highest or nearly highest SN ratio for the target component in the target sample can be obtained, so that an analysis with high accuracy and high sensitivity can be performed.

Figure 6:
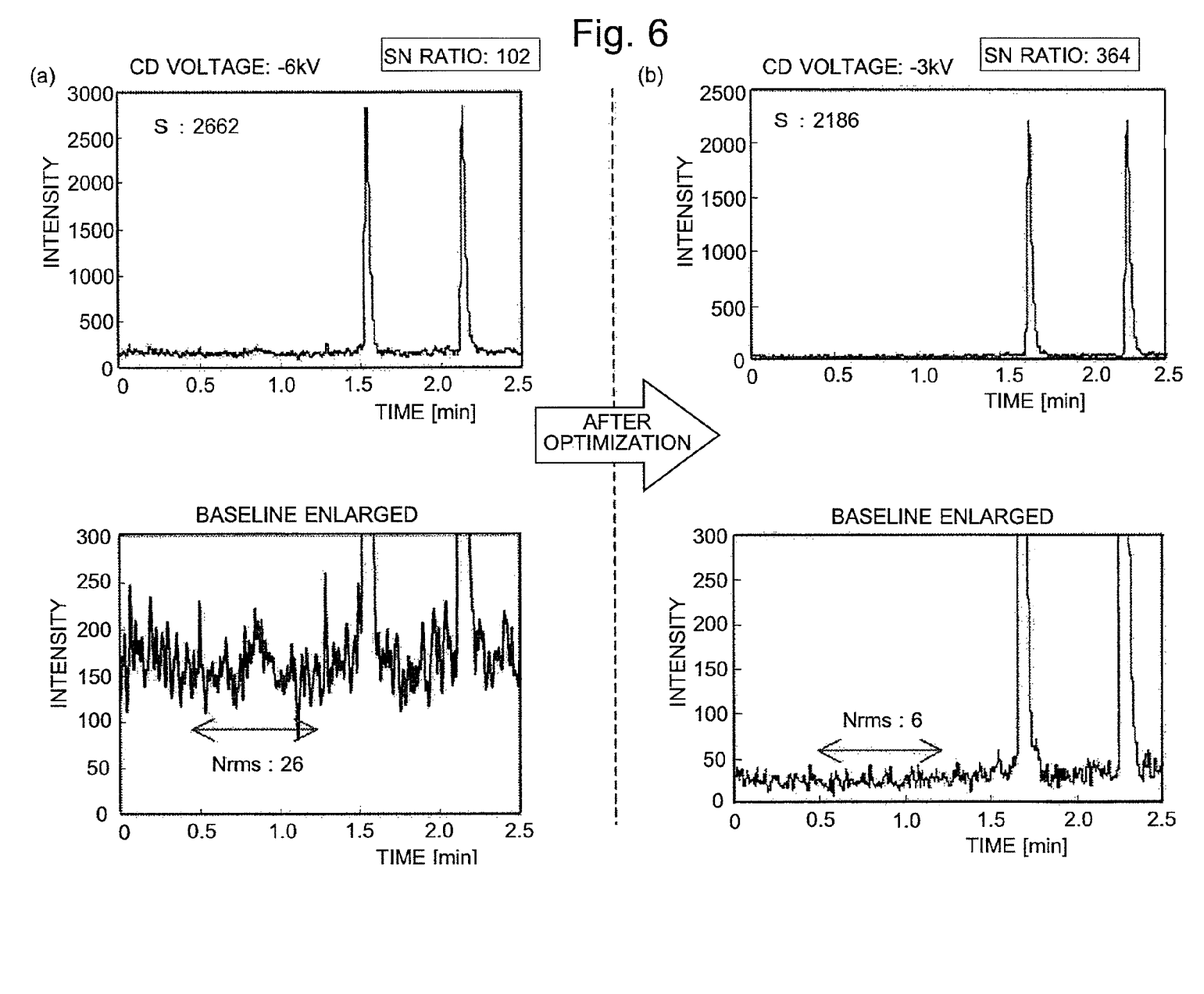
FIG. 6 shows an example of an actual measurement for explaining the effect of the CD voltage optimization process.

FIG. 6 shows a comparison of (a) a mass chromatogram obtained by an actual measurement with the CD voltage fixed at −6 kV and (b) a mass chromatogram obtained after the previously described CD voltage optimization process was performed. As a result of the CD voltage optimization process in which the CD voltage was set at −3 kV, the SN ratio was improved from 102 to 364. Thus, with the LC/MS of the present embodiment, it is possible to obtain detection signals with high SN ratios by appropriately regulating the CD voltage according to the analysis conditions at that point in time and/or the mass-to-charge ratio of the ion to be analyzed.

As is evident from the previous descriptions, in the LC/MS of the present embodiment, the CD voltage at which the SN ratio is maximized or nearly maximized must be found for each different setting of the analysis conditions including the LC separation condition and the mass-to-charge ratio of the ion to be analyzed. Therefore, if any analysis condition is changed, or if an ion having a different mass-to-charge ratio is to be analyzed, it is basically necessary to once more search for the optimum CD voltage. However, even after some condition is changed, the optimum CD voltage selected before that change can still be used if that change neither affects the conditions under which droplets are formed by being sprayed from the spray nozzle 21 in the MS unit 2 nor affects the conditions for the formed droplets to reach the ion detector 29 without disappearing during their travel.

In the previous descriptions, it is assumed that the target sample contains a single target component. Even in the case of a target sample containing a plurality of target components, it is possible to find an optimum CD voltage for each of the target components temporally separated in the LC unit 1 by determining the ion intensity of an ion originating from each component and calculating the SN ratio.

Normally, the CD voltage switching time, inclusive of the time waiting for the stabilization of the CD voltage after the voltage-switching operation, is approximately within a range from 15 to 20 msec. Therefore, by providing a waiting time of approximately 15 to 20 msec between the actual measurement times (ion detection times), it is possible to sequentially obtain ion intensities corresponding to multiple levels of CD voltages. Accordingly, in the case where the elution of the target sample continues for a comparatively long period of time due to the LC separation conditions or other factors, and particularly, if the situation in which the concentration of the target component in the liquid sample is approximately at equal levels continues for more than a certain length of time (i.e. if the peak on the mass chromatogram has a broadened peak top), it is possible to sequentially change the CD voltage to multiple levels and obtain the ion intensity signal for each CD voltage while the concentration of the target component is approximately at equal levels. According to this method, it is unnecessary to perform the LC/MS analysis a plurality of times with the same target sample injected each time as in the previous embodiment, so that the time required for the CD voltage optimization process will be shorter and the amount of sample used will be smaller.

The previous embodiment is an example of the present invention applied in an LC/MS. The present invention can also be applied in a mass spectrometer having no means for component separation, such as the LC. One example is an atmospheric pressure ionization mass spectrometer having the configuration of introducing a sample by a flow injection method. A problem similar to the previously described one occurs in this type of system, and similar effects can be obtained by applying the present invention.

It is evident that any change, modification or addition appropriately made within the spirit of the present invention in any respects other than the previously described ones will also be included within the scope of claims of the present application.

REFERENCE SIGNS LIST

1 . . . Liquid Chromatograph (LC) Unit
10 . . . Mobile Phase Container
11 . . . Liquid-Sending Pump
12 . . . Injector
13 . . . Column
2 . . . Mass Spectrometer (MS) Unit
20 . . . Ionization Chamber
21 . . . Spray Nozzle
22 . . . Desolvation Tube
23 . . . First Intermediate Vacuum Chamber
24 . . . First Ion Guide
25 . . . Second Intermediate Vacuum Chamber
26 . . . Second Ion Guide
27 . . . Analysis Chamber
28 . . . Quadrupole Mass Filter
29 . . . Ion Detector
291 . . . Conversion Dynode
292 . . . Secondary Electron Multiplier
293 . . . CD Voltage Generator
3 . . . Data Processing Unit
31 . . . A/D Converter
32 . . . Data Collector
33 . . . SN Ratio Calculator
34 . . . Optimum CD Voltage Determiner
4 . . . Analysis Control Unit
41 . . . CD Voltage Optimization Controller
42 . . . Optimum CD Voltage Memory
5 . . . Central Control Unit
6 . . . Operation Unit
7 . . . Display Unit

The invention claimed is:

1. A mass spectrometer having: an ion source for ionizing a component in a sample; a mass analyzer for separating ions generated by the ion source according to their mass-to-charge ratios; and an ion detector for detecting the ions separated by the mass analyzer, the ion detector having a conversion dynode for converting ions into electrons and a secondary electron multiplier for multiplying and detecting the electrons, the mass spectrometer comprising:
   a) a voltage supplier for applying high voltage to the conversion dynode, where the high voltage is independent from a voltage applied to other components of the mass spectrometer;
   b) an analysis executer for changing the voltage applied to the conversion dynode by the voltage supplier to a plurality of levels, and for obtaining, for every change in the voltage applied to the conversion dynode, a noise signal under an analysis condition at that point in time and a detection signal corresponding to an ion originating from a target component; and
   c) an optimum voltage setter for calculating an SN ratio based on the noise signal and the detection signal obtained by the analysis executer for each different level of the applied voltage, and for determining, based on the calculated result, the voltage to be applied to the conversion dynode in an analysis of the target component.

2. The mass spectrometer according to claim 1, wherein the ion source is an atmospheric pressure ion source for ionizing a component in a sample in liquid form.

3. The mass spectrometer according to claim 2, wherein a liquid sample separated into components by a liquid chromatograph is introduced into the atmospheric pressure ion source.

* * * * *